(12) United States Patent
Tadin

(10) Patent No.: US 6,493,958 B1
(45) Date of Patent: Dec. 17, 2002

(54) METHOD AND APPARATUS FOR MEASURING FOOT GEOMETRY

(75) Inventor: Tony G. Tadin, Woodside, CA (US)

(73) Assignee: Amfit, Inc., Santa Clara, CA (US)

( * ) Notice: Subject to any disclaimer, the term of this patent is extended or adjusted under 35 U.S.C. 154(b) by 152 days.

(21) Appl. No.: 09/692,015

(22) Filed: Oct. 19, 2000

Related U.S. Application Data

(60) Provisional application No. 60/164,090, filed on Nov. 6, 1999.

(51) Int. Cl.[7] .................................................. A61B 5/103
(52) U.S. Cl. ........................................ 33/515; 33/514.2
(58) Field of Search ............................... 33/515, 514.2, 33/1 BB, 512; 12/16, 21

(56) References Cited

U.S. PATENT DOCUMENTS

| | | | | |
|---|---|---|---|---|
| 2,330,317 A | * | 9/1943 | Stewart | 33/515 |
| 2,472,754 A | * | 6/1949 | Mead | 33/515 |
| 4,998,354 A | * | 3/1991 | Silverman et al. | 33/514.2 |
| 5,390,680 A | * | 2/1995 | Brenner | 33/515 |

* cited by examiner

*Primary Examiner*—Christopher W. Fulton
(74) *Attorney, Agent, or Firm*—Ohlandt, Greeley, Ruggiero & Perle, L.L.P.

(57) ABSTRACT

An apparatus and method for measuring a plantar contour having a foam impression block and a carrier. The apparatus has a foam impression block including a front portion and a rear portion and a carrier including a height adjuster. The block is associated with the carrier such that the rear portion and the height adjuster are adjacent one another.

70 Claims, 11 Drawing Sheets

METHOD AND APPARATUS FOR MEASURING FOOT GEOMETRY

RELATED APPLICATION

This application claims priority of U.S. Provisional Application No. 60/164,090, filed on Nov. 6, 1999, the disclosure of which is incorporated herein by reference.

BACKGROUND OF THE INVENTION

1. Field of the Invention

The present invention relates to an apparatus and method of use for measuring the geometry of a foot in the position the foot will be in when inside of a shoe. More particularly, the present invention relates to an apparatus having a foam impression block specially formed into the shape the target foot wear will have. Moreover, the present invention relates to methods of using such an apparatus for measuring the plantar contour and instep of a foot in the position the foot will be in when inside of a shoe.

2. Description of the Related Art

A number of methods currently exist to measure the geometry of the plantar contour of a foot. The accurate measurement of the plantar contour is used in the manufacture of custom insoles. The prior art methods include plaster casting, optical scanning, contact sensor measurement, as well as foam impression measurement. These methods require the foot to be in a planar position. However, some shoes, such as high heels or other shoes with a slope, distort the plantar contour and instep due to the shifting of the user's body weight. Accordingly, the insoles made using these prior art methods do not account for such distortions. Moreover, these prior art methods are not well suited for home use.

The optical scanning methods and contact sensor measurement methods utilize expensive equipment. These methods provide an accurate and complete measurement of the foot. But, the size, expense and complexity of the equipment necessary for these methods makes them not suitable for use in all locations. Moreover, these methods do not permit accurate measurement of the geometry of the foot in the position it will be in when inside of a shoe.

Plaster casting methods require the measurement to be performed by a person other then the one being measured. This method provides an accurate and complete measurement of the foot but can be very messy and time consuming. Thus, plaster casting methods are not suitable for use in a person's home or by one's self. Moreover, these methods do not permit accurate measurement of the geometry of the foot in the position it will be in when inside of a shoe.

Foam impression measurement methods and apparatus utilize an easily deformable foam block. A person steps onto the block, thus crushing the foam in the locations of higher pressure. In this manner, the foam block deforms in the approximate shape of the persons' plantar contour. While this prior art method may be suitable for home use, it produces a sub-optimal characterization of the foot for a number of reasons. First, the foam block is uniform in thickness from heel to toe. This causes the toes to be forced upward as the foot is pressed into the foam because the toes of the foot have substantially less pressure on them than the region of the foot from the heel to the metatarsal heads. Forcing the toes upward can cause a number of problems including, hyper-extension of the plantar fascia, lowering of the correct arch height, and improper measurement of the forefoot and heel. Second, under full body weight, the foot expands allowing for a larger than normal foot impression. Additionally, the prior art does not provide for measurement of the instep. Moreover, the current foam materials and methods do not permit accurate measurement of the geometry of the foot in the position it will be in when inside of a shoe.

In the manufacture of custom insoles, the use of the plaster casting and foam impression methods also require the use of a scanning system. The scanning system may act directly on the negative impression within the foam or plaster. Scanning systems that act directly on negative impressions are known in the art. These laser scanning systems consist of a laser with a line generating optic. The laser projects a line at a know incident angle onto the negative impression. A camera is used to read the position of the laser line on the negative impression. Alternatively, the scanning system may act on a positive plaster model made from the negative impression within the plaster or foam. Scanning systems that act directly on the positive impressions are also known in the art. One such scanning system, provided by U.S. Pat. No. 4,876,758, specially constructed array of pin-like sensors. In either circumstance, the scanning system is used to digitize the measured contour. The digitized contour is provided to a computer controlled milling machine. The milling machine uses the digitized information to manufacturing a custom insole matching the digitized contour. Accordingly, the apparatus and methods of the present invention provide for cheaper and easier means to provide custom manufactured insoles to a customer.

Accordingly, it is an object of the present invention to provide foot measurement apparatus and methods, which overcome the limitations set forth above.

SUMMARY OF THE INVENTION

It is an object of the present invention to provide an apparatus for measuring a plantar contour. The apparatus has a foam impression block, and a carrier having a heel. The block has a toe thickness, a length and a heel thickness. The toe thickness is less than the heel thickness. The block is disposed upon the carrier such that the heel thickness and the heel are adjacent one another.

It is a further object of the present invention to provide an apparatus for measuring a plantar contour and an instep. The apparatus has a foam impression block and a carrier. The carrier has a heel and a plurality of straps. The block has a toe thickness, a length and a heel thickness wherein the toe thickness is less than the heel thickness. The block is disposed upon the carrier such that the heel thickness and the heel are adjacent one another. The plurality of straps are disposed upon the carrier and are adapted to wrap around the instep such that a plurality of sizing graduations disposed upon each of the straps are readable.

It is also an object of the present invention to provide a method for measuring the plantar contour of a foot. The method having the steps of: (1) placing the plantar contour over a foam impression block disposed upon a carrier having a heel wherein the block has a toe thickness, a length and a heel thickness, the toe thickness is less than the heel thickness, and the block is disposed upon the carrier such that the heel thickness and heel are adjacent one another; (2) aligning the toes with the toe thickness; and (3) urging the plantar contour into the block to deform the block.

It is a further object of the present invention to provide a method for measuring the plantar contour and instep of a foot. The method having the steps of: (1) placing the plantar contour over a foam impression block disposed upon a carrier having a heel and a plurality of straps, wherein the block has a toe thickness, a length and a heel thickness, the toe thickness is less than the heel thickness, the block is disposed upon the carrier such that the heel thickness and the heel are adjacent one another, and the plurality of straps are disposed upon the carrier are adapted to wrap around the foot; (2) aligning the toes of the foot with the toe thickness; (3) urging the plantar contour into the block to deform the block; (4) wrapping the straps around the instep such that a plurality of sizing graduations disposed upon each of the straps are readable; and (5) noting the sizing graduation indicated by each of the straps.

BRIEF DESCRIPTION OF THE DRAWINGS

FIG. 11b is a side view of the dual density embodiment of FIG. 11a.

DESCRIPTION OF THE PREFERRED EMBODIMENT

Figure 1:
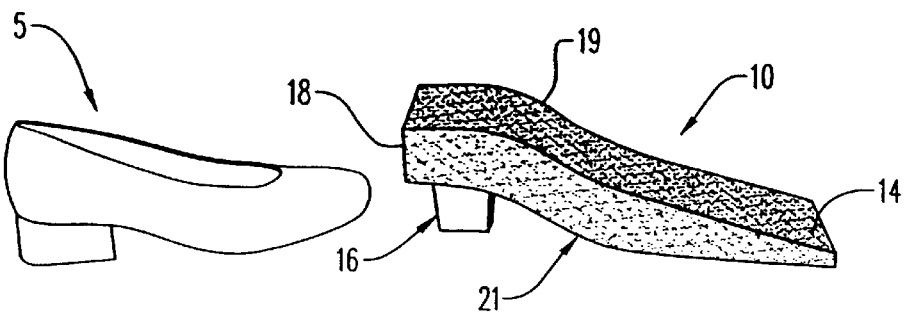
FIG. 1 is a side perspective view of a first embodiment of the foam block of the present invention.

Referring to the figures and more particularly to FIG. 1, a foam impression block is shown and is generally designated by the number 10. Block 10 is made from pressure sensitive materials, which compress when a person's foot is pressed into the block. Preferably, block 10 comprises a foam casting material having low density, high flexural modulus and low shear strength. Accordingly, block 10 provides a material, which is easily deformed, with little or no memory, and retains the deformed shape indefinitely. Expanded phenolic materials such as those commonly used for insulation and ultra low density expanded polystyrene are suitable for block 10. In the preferred embodiment, block 10 is expanded phenolic material.

Block 10 has a hardness or density from about 2 to about 25 pounds per square inch (hereinafter"psi"). Selection of the correct foam density depends on factors such as body weight, lifestyle or desired usage (e.g., sport, casual, or formal). For example, a density of about 2 psi is selected for casting a foot in block 10 while in the sitting position, a density of about 5 psi is selected for casting a foot in block 10 while in standing position, and a density of about 10 psi is selected for taking a dynamic casting of a foot in block 10 as described hereinbelow.

Shown in FIG. 1, block 10 has a toe thickness 14, a heel 16, a heel thickness 18, and a length 19. In one embodiment, toe thickness 14 and heel thickness are the same. In the preferred embodiment, toe thickness 14, heel thickness 18 and length 19 provide the block with a wedge-like shape. In this embodiment, toe thickness 14 is less than heel thickness 18, which minimizes any tendency for the toes of a person's foot to lift up while being pressed into block 10. For instance in a first embodiment, heel thickness 18 is in a range from about 20 mm to about 35 mm and toe thickness 14 is in a range from about 10 mm to about 15 mm. In the preferred embodiment, heel thickness 18 is approximately 35 mm and toe thickness 14 is approximately 10 mm.

Block 10 is disposed upon the top of carrier 21. Carrier 21 includes a heel 16 disposed on the bottom of the carrier. Heel 16 provides carrier 21 with a shape similar to a woman's shoe 5. Block 10 is disposed upon carrier 21 such that heel thickness 18 and heel 16 are adjacent to one another.

Figure 2:
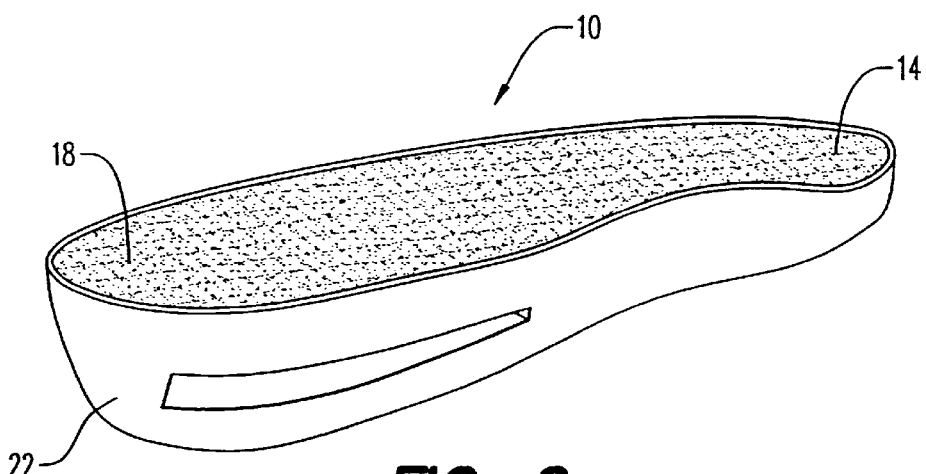
FIG. 2 is a rear perspective view of a second embodiment of the foam block of the present invention.
Figure 11A:
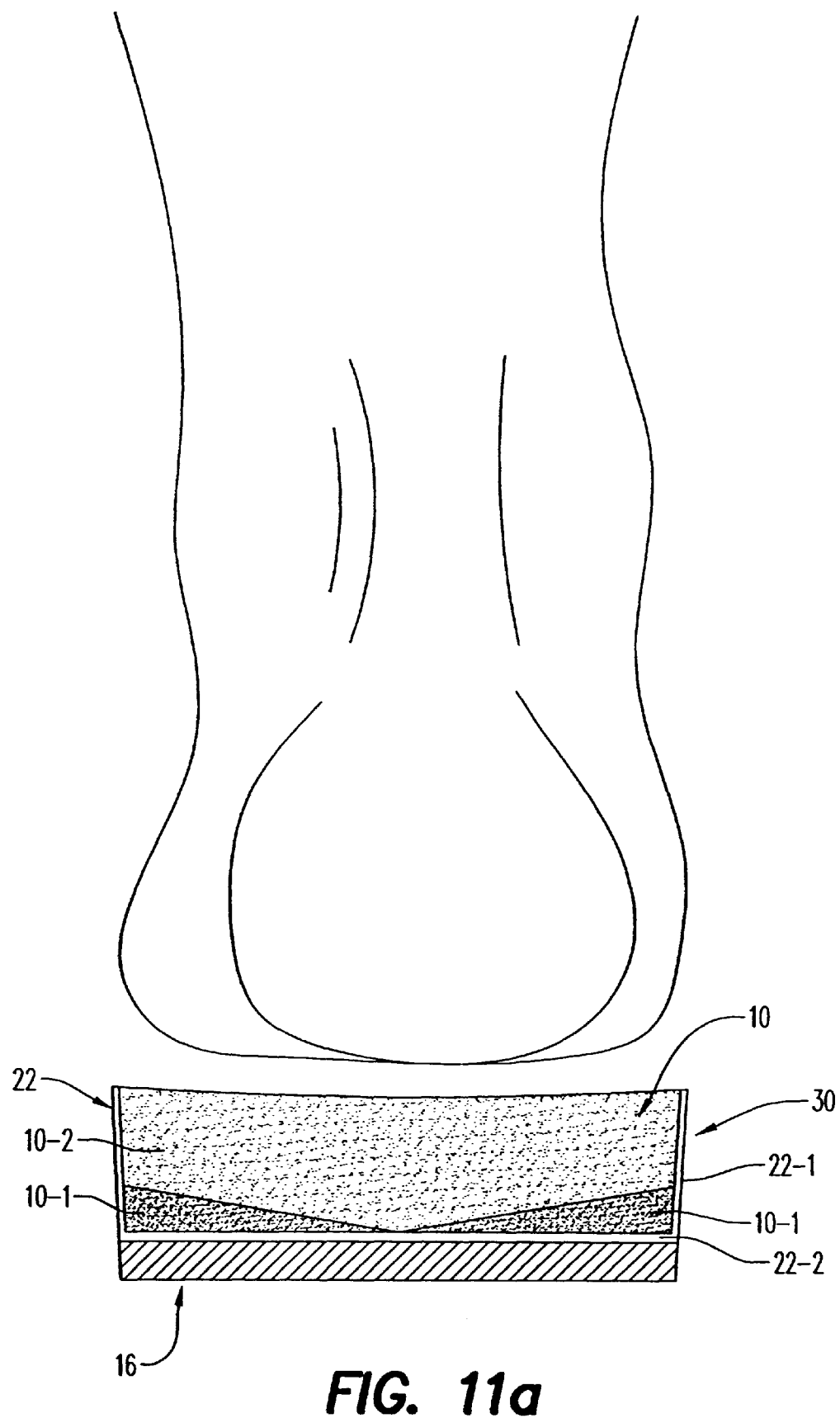
FIG. 11a is a rear view of a foot being placed into a dual density embodiment of the present invention.

Heel 16 improves the accuracy of the measurement of a person's foot using block 10. Heel 16 and carrier 21 by more closely approximating the position and shape a foot assumes when wearing the desired shoe. An alternate embodiment of heel 16, shown in FIG. 2, the slope of a man's shoe is approximated. In this embodiment, heel 16 and carrier 21 form an integral container 22. In yet another embodiment of heel 16, shown in FIG. 3, the slope of a sneaker or tennis shoe is approximated. In this embodiment, heel 16 and carrier 21 form integral container 22. In yet another embodiment, block 10 is provided with heel 16 having an adjustable height. The height of heel 16 is adjustable from (1) a heel height less than the toe height, providing a negative slope to block 10; (2) a heel height equal to the toe height, providing no slope to block 10; (3) a heel height more than the toe height, providing a positive slope to block 10. Preferably, container 22 is shaped so as to approximate the visual appearance of the exterior of a sole of a shoe. Moreover, the inside of container 22 is shaped having side-walls 22-1 at about a ninety degree angle with respect to its bottom surface 22-2 as shown in FIG. 11a, or having side-walls 22-1 with a radius with respect to its bottom 22-2 as shown in FIG. 3c.

Figure 3:
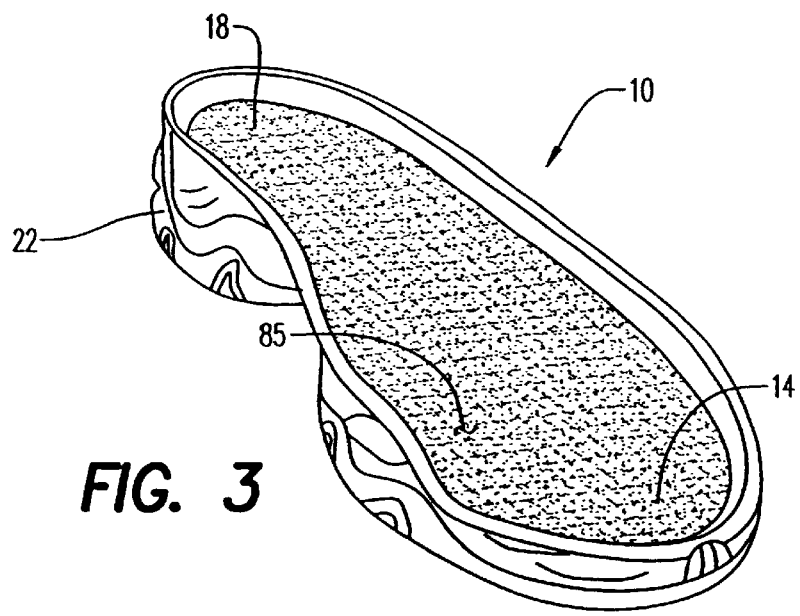
FIG. 3 is a front perspective view of a third embodiment of the foam block of the present invention.
Figure 3A:
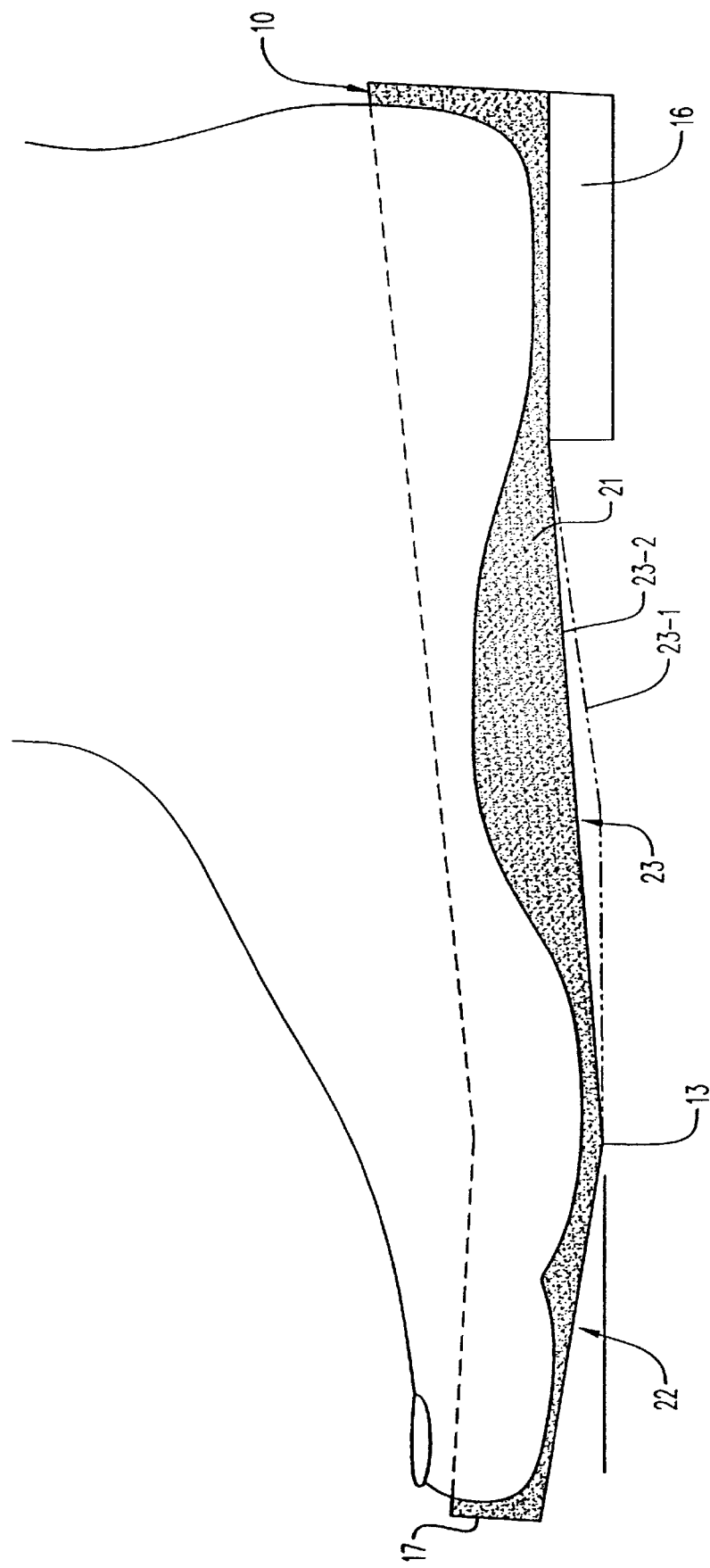
FIG. 3a is a side view of a foot being placed on an embodiment of the foam block of FIG. 1.
Figure 3B:
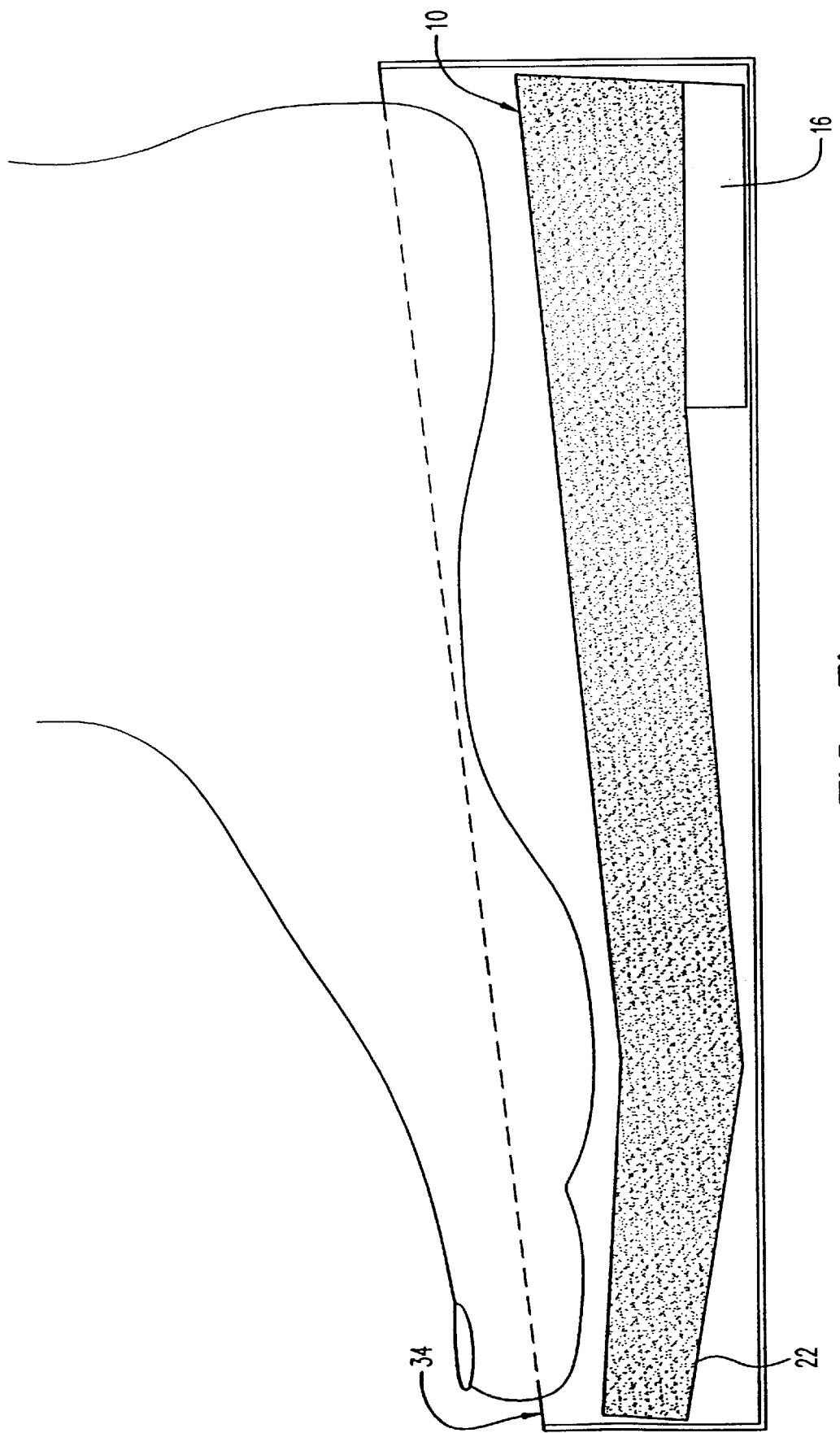
FIG. 3b is a side view of a foot being placed on an alternate embodiment of the container of FIG. 2.
Figure 3C:
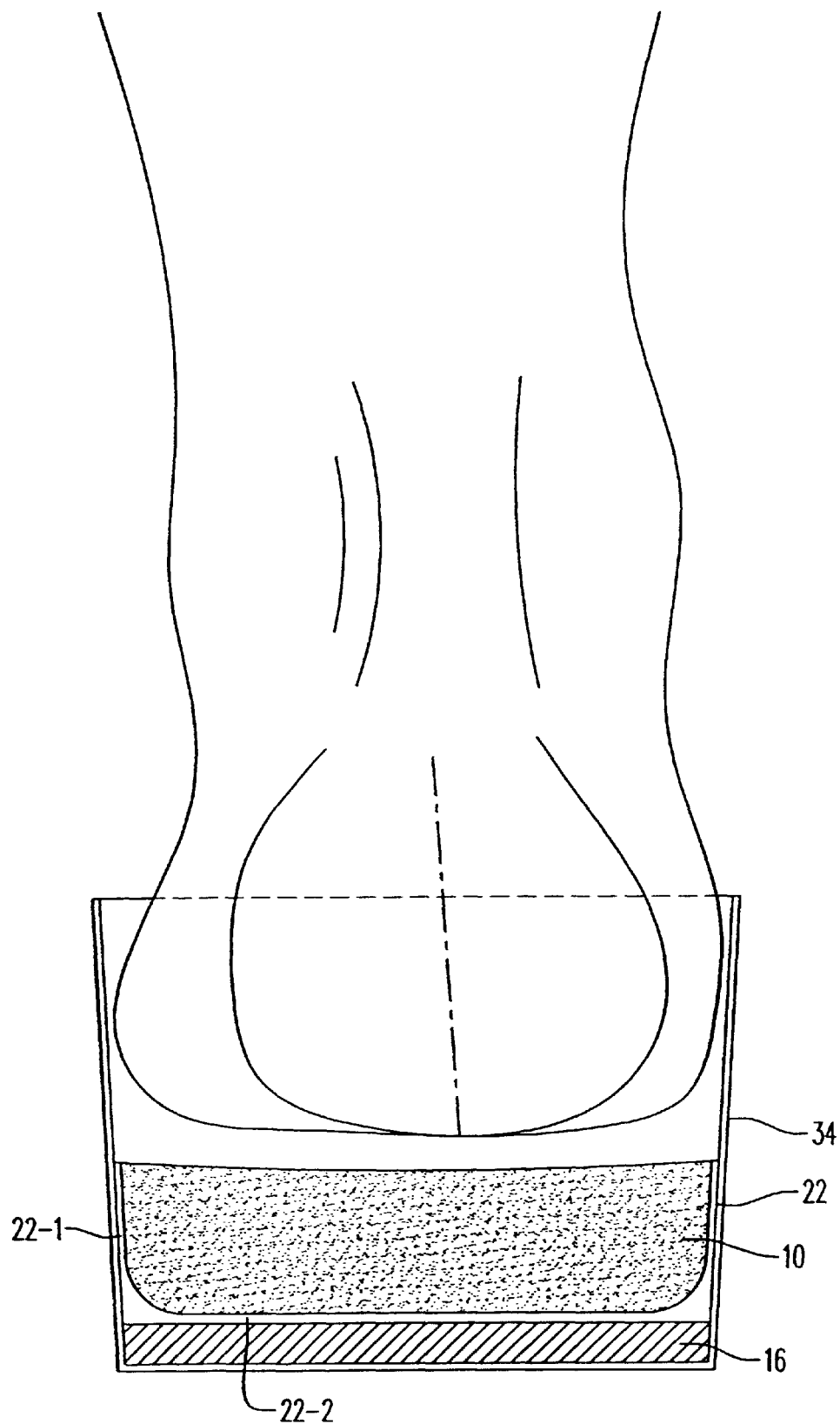
FIG. 3c is a rear view of a foot being placed on the container of FIG. 3b.

In an alternate embodiment of FIGS. 3b and 3c, container 22 includes a vertical guide portion 34. Portion 34 extends upwardly from container 22 above the level of block 10. Accordingly, portion 34 aids the user to align the foot with regards to block 10.

In an alternative embodiment, carrier 21 and/or container 22 act to provide flexure to block 10. In this embodiment shown in FIG. 3a, carrier 21 includes a biasing section 23. Biasing section 23 is positioned between heel 16 and toe portion 17. Preferably, biasing section 23 is positioned between heel 16 and foot pivot point portion 13. Biasing section 16 elastically flexes or biases under the weight of the user shown as position 23-1 and returns to its original position after use shown as position 23-2. Accordingly, biasing section 23 further improves the accuracy and support of the measurement of a person's foot in a weighted position using block 10. In another alternate embodiment, the amount of flexure in biasing section 23 is adjustable. The amount of flexure in biasing section 23 is adjustable either along the length of the foot, along the width of the foot, or along a combination of the length and width.

It should be recognized that combinations of heel 16, carrier 21 and/or biasing section 23 which more closely approximates the position of the foot wearing the shoe is included within the scope of the present invention.

Figure 4:
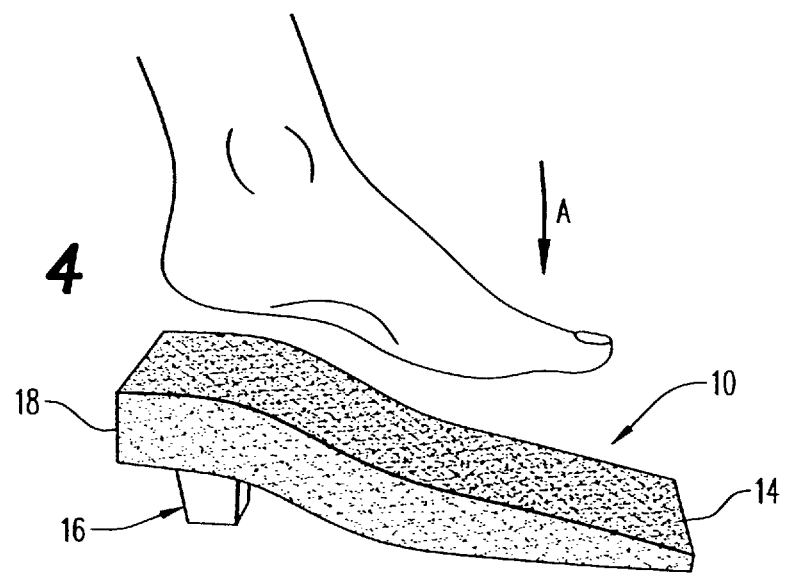
FIG. 4 is a side perspective view of a foot being placed on the foam block of FIG. 1.
Figure 5:
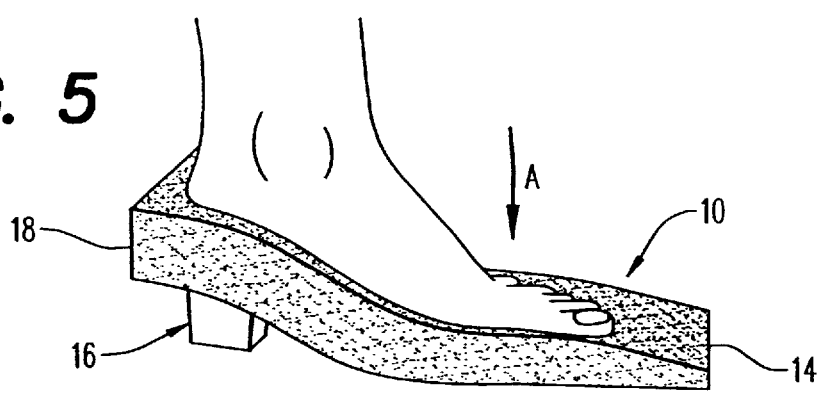
FIG. 5 is a side perspective view of the foot fully deforming the foam block of FIG. 1.
Figure 6:
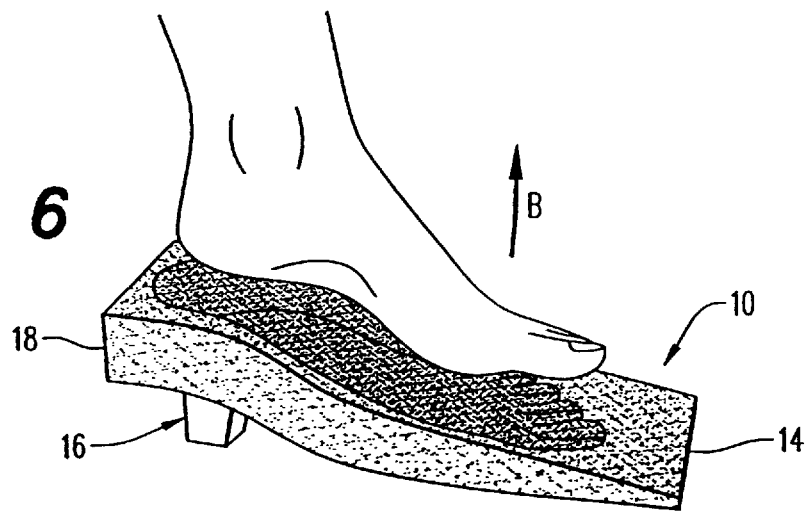
FIG. 6 is a side perspective view of the foot being removed from the deformed foam block of FIG. 1.
Figure 7:
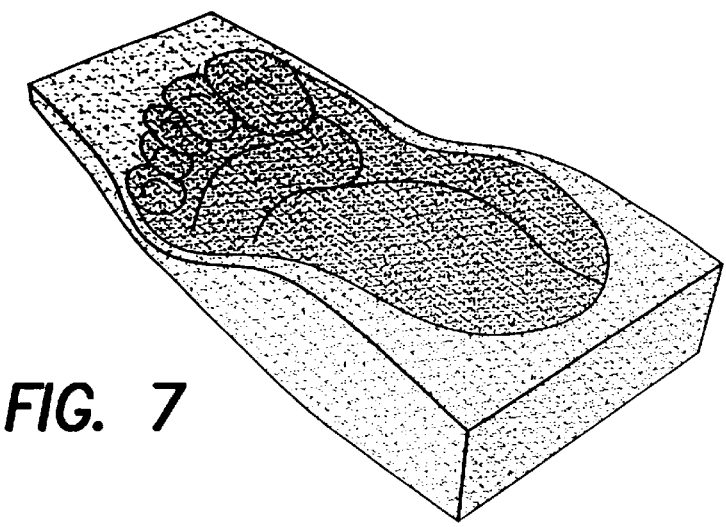
FIG. 7 is a rear perspective view of the deformed foam block of FIG. 1 after the foot has been removed.

By way of example, the use of block 10 to measure a person's plantar contour is described below with reference to the embodiment of block 10 shown in FIG. 1. The user positions one foot over block 10 with their toes toward toe thickness 14 and their heel towards heel thickness 18 and moves their foot towards block 10 in the direction shown by arrow A, shown in FIG. 4. Next, the user applies weight to that foot in the direction shown by arrow A until block 10 is fully deformed, shown in FIG. 5. The user's foot, with weight applied thereon, will conform to the shape the foot has when wearing a shoe having a heel height substantially equal to the height of heel 16. Thus, block 10 will deform in the shape the user's foot will assume when wearing the shoe. Next, the user removes that foot from deformed block 10 in the direction shown by arrow B, shown in FIG. 6. A fully deformed block 10, having the shape of the person's foot will conform to when wearing the shoe, is shown in FIG. 7.

In an alternative embodiment of the present invention, block 10 has been modified to provide for measurement of the instep or top surface of the foot. This information is often also required to properly fit footwear. A person with a "high instep" would require a shoe that is deeper and may prevent the person from properly fitting into snugger fitting footwear. Further, by knowing the instep of a subject foot and knowing the internal geometry of a particular shoe, it is possible to determine if the shoe will fit properly. This information is vital when manufacturing custom plantar contours. For instance, if it is known via measurement using the present invention that there will be 2 mm of extra space in the shoe, it is possible to tailor the characteristics of the plantar contours to take up this extra space.

Figure 8:
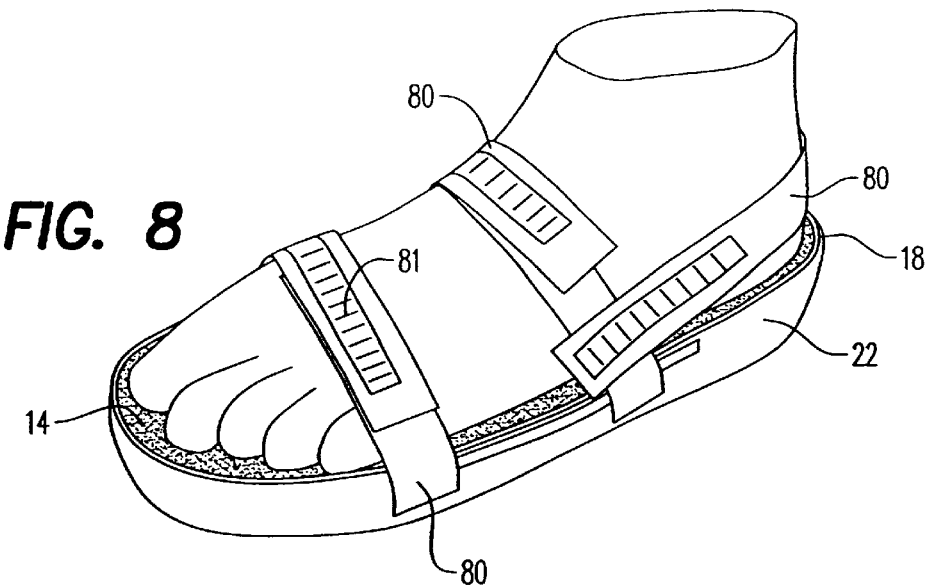
FIG. 8 is a front perspective view of the deformed foam block of FIG. 2 showing an instep measurement embodiment.

A plurality of straps 80 are used to characterize the instep, as shown in FIG. 8. Each strap 80 has a plurality of graduations 81 on its top surface indicating instep range. Each strap 80 is disposed upon carrier 21 or container 22 and is run over the top of the foot, and the instep range is read off of graduations 81. As an additional feature, straps 80 secure block 10 to the person's foot such that the person can walk with the block secured to their foot. Thus, straps 80 enable dynamic casting of the foot. The shifting in body weight and the changing of foot size, which occur as a result of walking, will therefore be captured by block 10. Dynamic casting of the foot requires block 10 to have a density of at least 3psi.

Figure 9:
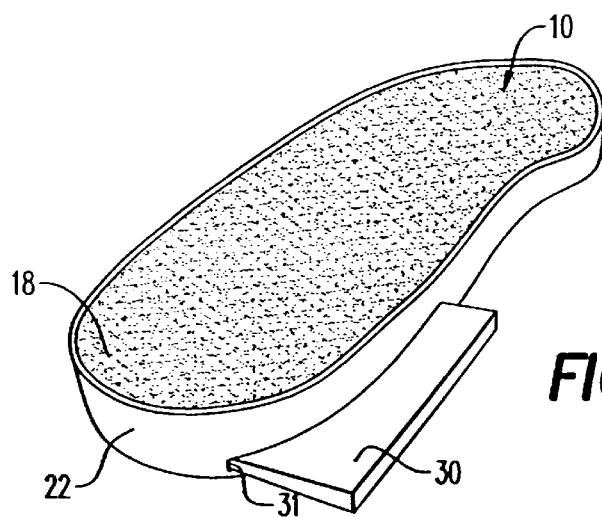
FIG. 9 is a rear perspective view of the foam block of FIG. 2 showing a wedge correction embodiment.

It is oftentimes desirable to make adjustments to the position of the foot. For instance, it is often desirable to manipulate the angle that the plantar contour of the foot has with respect to the floor to correct for excessive pronation, supination or the like. In this instance block 10, as shown in FIG. 9, is further provided with a support 30. Support 30 is insertable between block 10 and support 21 to correct for pronation or supination of the foot or for difference in the length of the leg. Alternately, support 30 is insertable into a slot 31 defined within container 22. In another embodiment, support 30 is formed within carrier 21/container 22. Support 30 further improves the accuracy of the measurement of a person's foot by more closely approximating the position and shape their foot will assume when wearing the desired shoe having a desired level of pronation or supination correction.

Figure 10A:
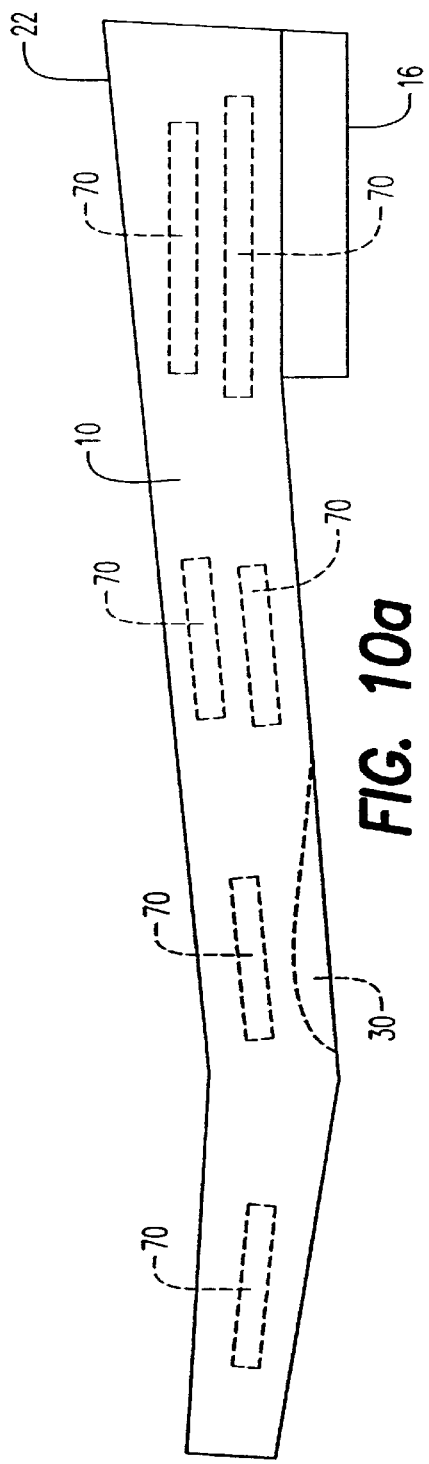
FIG. 10a is a side view of a first metatarsal support embodiment of the present invention.
Figure 10B:
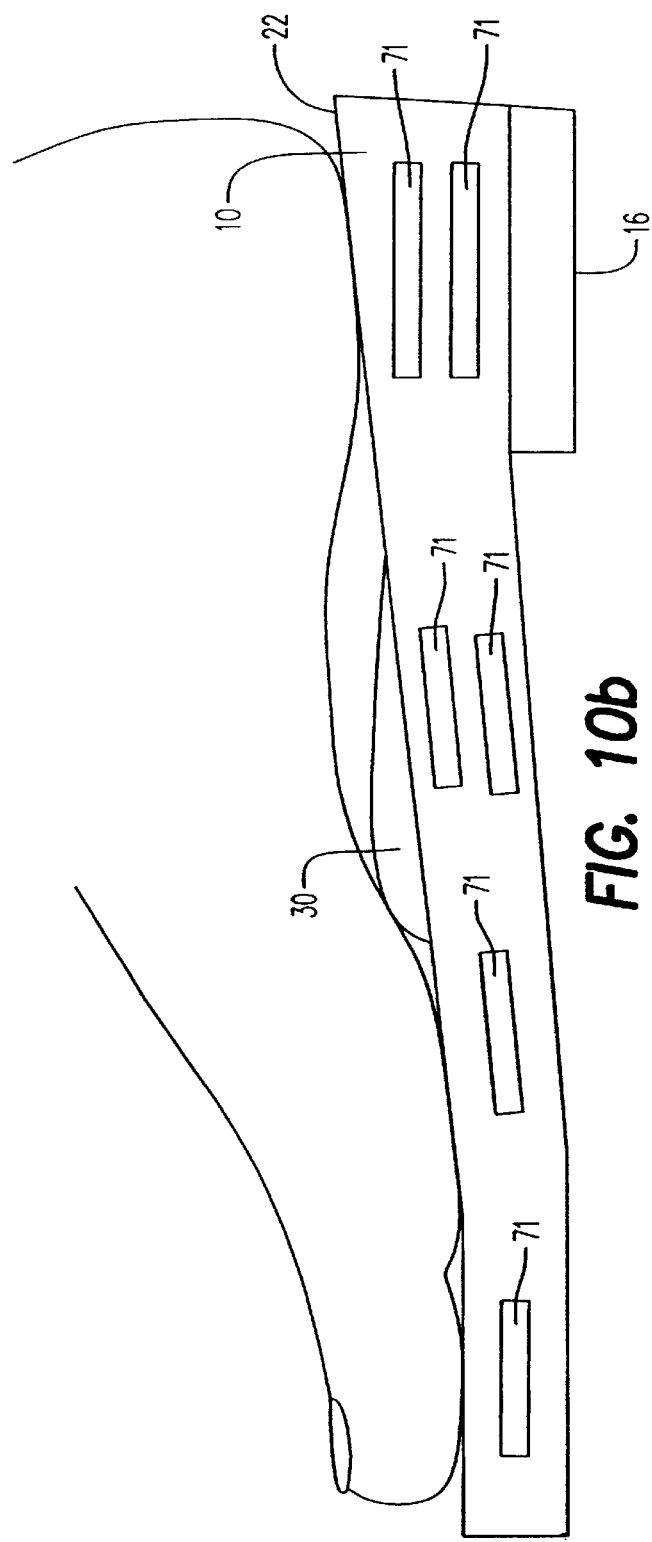
FIG. 10b is a side view of a second metatarsal support embodiment of the present invention.

In alternate embodiments, support 30 is a metatarsal support under block 10 shown in FIG. 10a or on block 10 as shown in FIG. 10b. Support 30, as a metatarsal support, further improves the accuracy of the measurement of a person's foot by more closely approximating the position and shape their foot will assume when wearing the desired shoe having a desired level of metatarsal support.

Figure 11B:
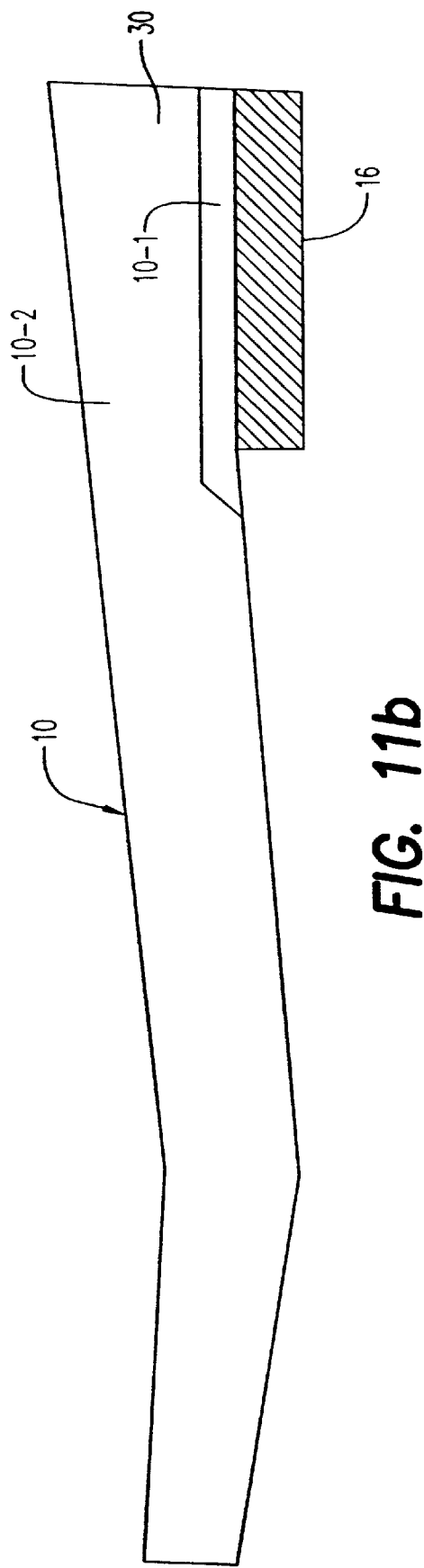

In yet another alternate embodiment shown in FIGS. 11a and 11b support 30 is provided by the selective use of various density foams within block 10. In this instance, block 10 includes a region 10-1 having a first density and a region 10-2 having a second lower density. Region 10-1, being of higher density, ensures that the heel of the user is properly centered within block 10. Support 30 further improves the accuracy of the measurement of a person's foot by more closely approximating the position and shape their foot will assume when properly centered. For instance, in a preferred embodiment region 10-1 has a density of 5 psi and region 10-2 has density of 3 psi. In this embodiment, the higher density of region 10-1 ensures that the foot is properly centered within the lower density region 10-2.

It should be recognized that support 30 which aids to adjust the foot within block 10 to more closely approximate the correct position of the foot wearing the shoe are included within the scope of the present invention.

Figure 12:
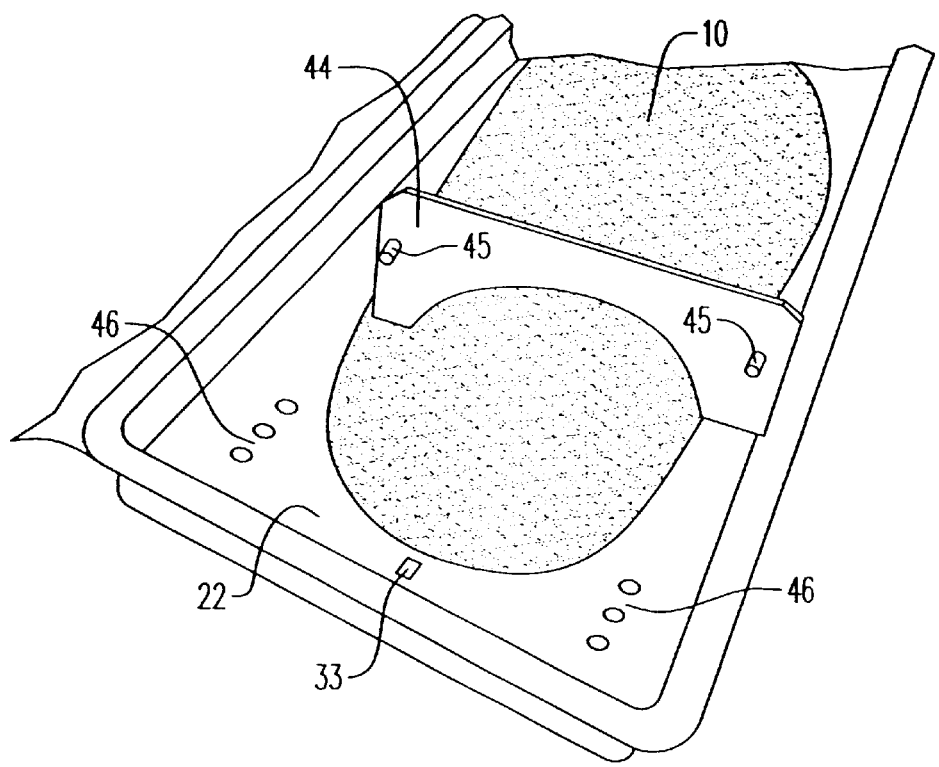
FIG. 12 is a perspective view of the heel guide embodiment of the present invention.

It is desirable for container 22 to be used for more than one shoe size. In the embodiments where support 30 is secured within container 22, the foot must be properly aligned over the support. Thus, a heel guide 44 shown in FIG. 12 is provided. Heel guide 44 enables container 22 to be used for more than one shoe size. Heel guide 44 is adapted to be removably coupled to container 22 in one or more positions such that the guide properly positions the foot of the user within the container. In a preferred embodiment, heel guide 22 includes studs 45 and container 22 includes recesses 46. Studs 45 are adapted couple with recesses 46 to removably secure heel guide 44 to container 22. Studs 45 are positioned on guide 22 and recesses 46 are positioned on container 22 so as to approximate the desired range of shoe sizes.

Shown in FIG. 3, a thin compliant medium 85, such as, but not limited to, terry cloth, is placed on top surface block 10. The foot is pressed into compliant medium 85, which in turn compresses block 10. Compliant medium 85 acts to prevent any of block 10 from adhering to the user's foot.

Figure 13:
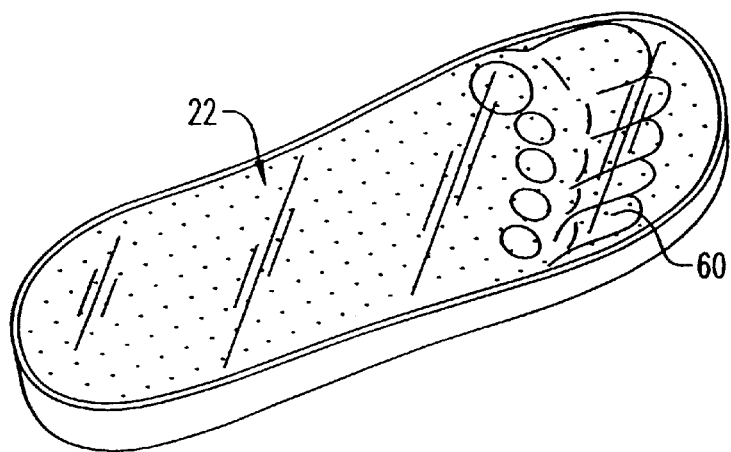
FIG. 13 is a perspective view of the clear embodiment of the container of the present invention.

It is oftentimes desirable to mark specific points on the bottom of foot where problems, such as a metatarsal head, exists. In this instance, it is desirable for container 22 to be of optically clear material as shown in FIG. 13. Optionally, only a portion of container 22 to be of optically clear material, such as bottom surface 22-2. Preferably, clear container 22 includes a reference grid 60 disposed thereon. Optionally, reference grid 60 is a Harris mat, a pedo bar graph, a grid that relates to computer display software for corrections or the like. Clear container 22 therefor enables the user to remove block 10 from container 22, to place their foot on reference grid 60 and precisely mark any existing problem spots.

Figure 14:
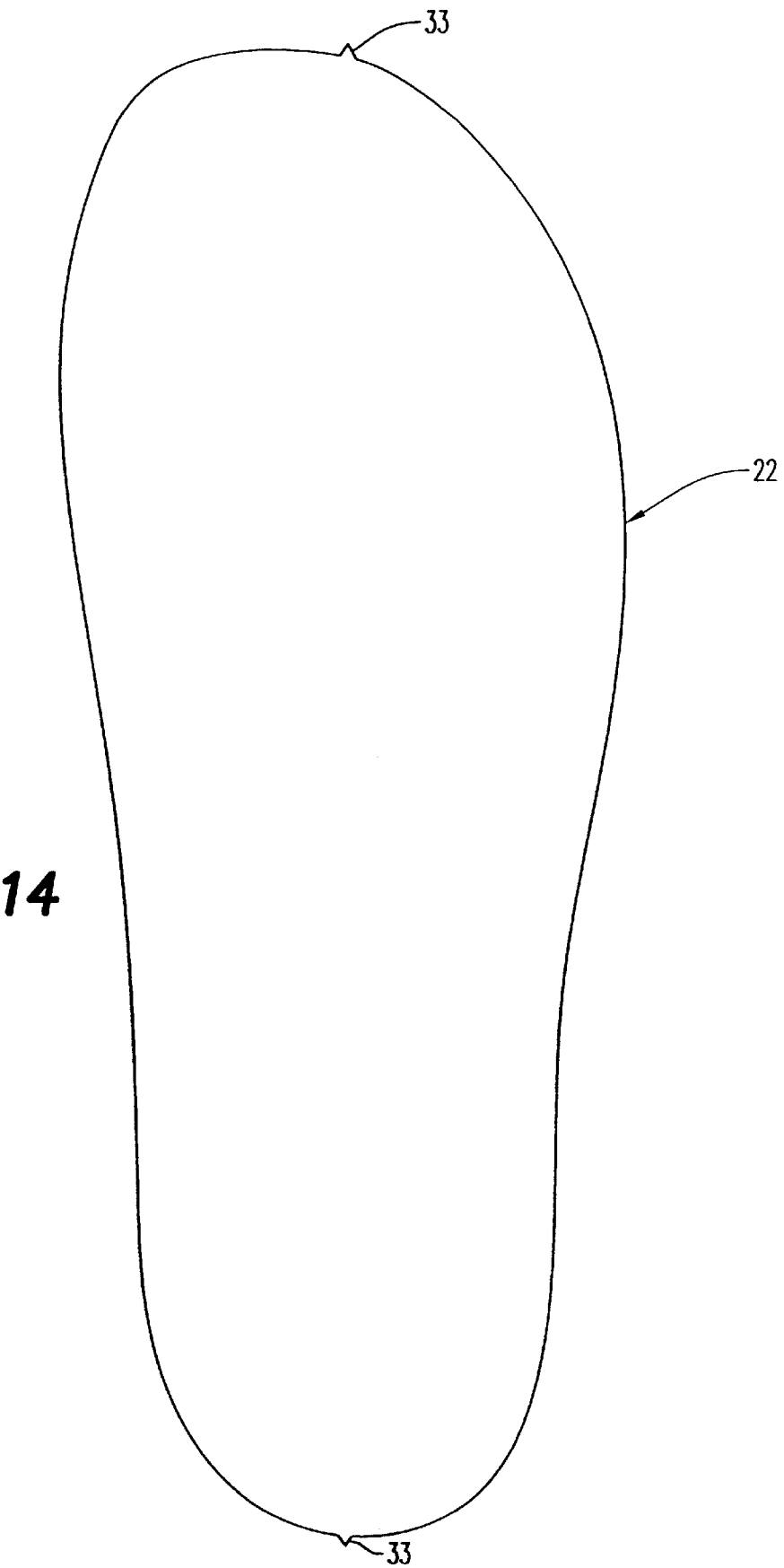
FIG. 14 is a top view of a scanning mark embodiment of the present invention.

As described above, the plantar contour measured by block 10 is often used in the manufacture of custom insoles. The process of converting the contour on block 10 into the custom insole often times requires using a scanner to digitize the contour directly from block 10. In this instance, it is desirable for carrier 21 and/or container 22 to include one or more scanning reference marks 33 as seen in FIGS. 12 and 14. Mark 33 assists the optical scanner in the fast and accurate centering of the container and measured plantar contour.

Optionally, container 22 and/or carrier 21 includes mechanisms to secure block 10 therein. For example, in a first embodiment an adhesive is used to secure block 10 within container 22. In alternate embodiments, indentations 70 (shown in FIG. 10*a*) or slots 71 (shown in FIG. 10*b*) are formed in container 22. Indentations 70 and/or slots 71 allow removal of block 10 prior to deformation of the block. However, once deformed by the user, block 10 expands into indentations 70 and/or slots 71 to secure the block in container 22.

It should be understood that the foregoing description is only illustrative of the invention. Various alternatives and modifications can be devised by those skilled in the art without departing from the invention. Accordingly, the present invention is intended to embrace all such alternatives, modifications and variances that fall within the scope of the appended claims.

What is claimed is:

1. An apparatus for measuring a plantar contour of a foot, comprising
   a permanently deformable impression block having a front portion and/or a rear portion, and
   a carrier wherein said impression block and said carrier form an integral container shaped to approximate the shape of a shoe sole.

2. The apparatus of claim 1, wherein said front portion has a toe thickness, said rear portion has a heel thickness, and said toe thickness is less than said heel thickness.

3. The apparatus of claim 2, wherein said heel thickness is in the range from about 20 mm to about 35 mm and said toe thickness is in the range from about 10 mm to about 15 mm.

4. The apparatus of claim 1, wherein said block is expanded phenolic foam.

5. The apparatus of claim 1, wherein said carrier further comprises height adjusting means adjacent either the front portion or rear portion.

6. The apparatus of claim 5, wherein said height adjusting means is capable of providing a slope to said block, said slope being in a range from a positive slope when said height adjusting means is adjacent the rear portion to a negative slope when said height adjusting means is adjacent the front portion.

7. The apparatus of claim 1, wherein said integral container has side walls at about a ninety degree angle with respect to its bottom surface.

8. The apparatus of claim 1, wherein said integral container has side walls having a radius with respect to its bottom surface.

9. The apparatus of claim 1, wherein at least a bottom portion of said integral container is clear.

10. The apparatus of claim 9, wherein said bottom portion further includes a reference grid adapted to precisely mark an identified spot of the plantar contour.

11. The apparatus of claim 1, wherein said carrier further includes a biasing section adapted to flex or bias during use.

12. The apparatus of claim 11, wherein the amount of flexion of said biasing section is adjustable.

13. The apparatus of claim 11, wherein said biasing section is positioned between a height adjusting means and a pivot point portion of said carrier, wherein said height adjusting means is adjacent either the front portion or rear portion.

14. The apparatus of claim 1, further comprising means to join said block and said carrier.

15. The apparatus of claim 14, wherein said joining means is adhesive.

16. The apparatus of claim 14, wherein said joining means is at least one slot within said container.

17. The apparatus of claim 14, wherein said joining means is at least one indentation within said container.

18. The apparatus of claim 14, wherein said joining means is an interference fit between said block and said container.

19. The apparatus of claim 1, further comprising means for manipulating the plantar contour.

20. The apparatus of claim 19, wherein said manipulating means is a wedge between said block and said carrier.

21. The apparatus of claim 19, wherein said manipulating means is a metatarsal support between said block and said carrier.

22. The apparatus of claim 19, wherein said manipulating means is a metatarsal support on said block.

23. The apparatus of claim 19, wherein said manipulating means comprises a first region of said block having a first density and a second region of said block having a second density.

24. The apparatus of claim 23, wherein said first density is lower than said second density.

25. The apparatus of claim 1, further comprising at least one scanning reference means disposed thereon for assisting an optical scanner to center said block within a scanning field.

26. The apparatus of claim 1, wherein said integral container further comprises vertical guide means disposed thereon for guiding the foot of a user into said block.

27. The apparatus of claim 1, wherein at least a bottom portion of said container is clear.

28. The apparatus of claim 27, wherein said bottom portion further includes a reference grid adapted to mark an identified spot of the plantar contour.

29. The apparatus of claim 1, wherein said integral container further includes an adjustable heel guide for positioning said foot within said integral container.

30. The apparatus of claim 1, wherein said foam impression block is disposed within a compliant medium.

31. An apparatus for measuring a plantar contour and an in step of a foot, comprising:
   a permanently deformable impression block saving a front portion and/or a rear portion,
   a container including carrier means, and
   at least one strap disposed upon said container and adapted to wrap around the instep.

32. The apparatus of claim 31, wherein said front portion has a front thickness, said rear portion has a rear thickness, and said front thickness is less than said rear thickness.

33. The apparatus of claim 31, wherein said at least one strap includes a plurality of sizing graduations disposed thereon such that said sizing graduations are readable when said at least one strap is wrapped around the instep.

34. The apparatus of claim 31, wherein said block is expanded phenolic foam.

35. The apparatus of claim 31, wherein said rear thickness is in the range from about 20 mm to about 35 mm and said front thickness is in the range from about 10 mm to about 15 mm.

36. The apparatus of claim 31, wherein said integral container includes height adjusting means capable of providing a slope to said block, said slope being in the range from a positive slope when said height adjusting means is adjacent the rear portion to a negative slope when said height adjusting means is adjacent the front portion.

37. The apparatus of claim 31, wherein said container is in the form of a shoe sole.

38. The apparatus of claim 31, wherein said carrier means further includes a biasing section adapted to flex or bias during use such that said block provides improved accuracy to the measurement of the plantar contour.

39. The apparatus of claim 31, further comprising means to join said block and said carrier.

40. The apparatus of claim 31, further comprising means for manipulating the plantar contour.

41. The apparatus of claim 40, wherein said manipulating means is a wedge between said block and said carrier means.

42. The apparatus of claim 40, wherein said manipulating means is a metatarsal support between said block and said carrier means.

43. The apparatus of claim 40, wherein said manipulating means is a metatarsal support on said block.

44. The apparatus of claim 40, wherein said manipulating means is a first region of said block having a first density and a second region of said block having a second density.

45. The apparatus of claim 44, wherein said first density is lower than said second density.

46. The apparatus of claim 31, further comprising at least one scanning reference means disposed thereon for assisting an optical scanner to center said block within a scanning field.

47. The apparatus of claim 31, wherein said container further comprises vertical guide means disposed thereon for guiding the foot of a user into said block.

48. The apparatus of claim 31, wherein said container further includes an adjustable heel guide for positioning said foot within said container.

49. The apparatus of claim 31, wherein said container further includes height adjusting means.

50. The apparatus of claim 49, wherein said impression block is associated with said carrier such that said height adjusting means is adjacent either the front portion or the rear portion.

51. A method for measuring the plantar contour of a foot, comprising:
    placing the plantar contour over a permanently deformable impression block associated with a carrier wherein said impression block has a front portion and a rear portion and wherein said impression block and said carrier form an integral container shaped to approximate the shape of a shoe sole;
    aligning the toes of the foot with said front portion, and
    urging the plantar contour into said block to deform said impression block.

52. The method of claim 51, wherein said front portion has a front thickness, said rear portion has a rear thickness, and said front thickness is less than said rear thickness.

53. The method of claim 51, further comprising securing said block to the foot via at least one strap associated with said carrier, and
    walking with said block secured to the foot to form a dynamic casting of the plantar contour.

54. The method of claim 51, further comprising inserting means for manipulating the plantar contour between said block and said carrier prior to placing the plantar contour over said foam impression block.

55. The method of claim 51, wherein said carrier further comprises height adjusting means.

56. The method of claim 55, wherein said impression block is associated with said carrier such that said height adjusting means is adjacent either the front portion or the rear portion.

57. A method for measuring the plantar contour and instep of a foot, comprising:
    placing the plantar contour over a permanently deformable impression block disposed upon a carrier having at least one strap adapted to wrap around the instep,
    wherein said impression block has a front portion and a rear portion,
    aligning the toes of the foot with said front portion, and
    urging the plantar contour into said block to deform said impression block,
    wrapping said at least one strap around the instep such that a plurality of sizing graduations disposed upon said at least one strap are readable, and
    noting said sizing graduation indicated by said at least one strap.

58. The method of claim 57, wherein said front portion has a thickness that is less than the thickness of said rear portion.

59. The method of claim 57, further comprising:
    securing said block to the foot via said at least one strap, and
    walking with said block secured to the foot to form a dynamic casting of the plantar contour.

60. The method of claim 57, wherein said carrier further includes height adjusting means.

61. The method of claim 60, wherein said block is associated with said carrier such that said height adjusting means is adjacent either said front portion or said rear portion.

62. A method for making a custom insole, comprising:
    measuring the plantar contour of a foot by placing the plantar contour over a permanently deformable impression block associated with a carrier wherein said impression block has a front portion and a rear portion, and said impression block and said carrier form an integral container shaped to approximate the shape of a shoe sole,
    aligning the toes of the foot with the front section;
    urging the plantar contour into the impression block to deform the impression block;
    digitizing the plantar contour provided by the deformed impression block using a scanner;
    providing the digitized plantar contour a computer controlled milling machine; and
    directing the computer controlled milling machine to manufacture the custom insole using the digitized contour.

63. The method of claim 62, wherein the front section is thicker than the rear section.

64. The method of claim 62, wherein measuring the plantar contour further comprises:
    securing the block to the foot via at least one strap associated with the carrier, and
    walking with the block secured to the foot to form a dynamic casting of the plantar contour.

65. The method of claim 62, wherein measuring the plantar contour further comprises:
    inserting means for manipulating the plantar contour between the block and the carrier.

66. The method of claim 62, wherein said carrier further comprises height adjusting means.

67. An apparatus for measuring a plantar contour, comprising a permanently deformable impression block having a front portion and/or a rear portion, and a carrier having a pivot point portion wherein said impression block and said carrier form an integral container shaped to approximate the shape of a shoe sole.

68. An apparatus for measuring a plantar contour, comprising a permanently deformable impression block having a front portion and/or a rear portion, a carrier wherein said impression block and said carrier form an integral container shaped to approximate the shape of a shoe sole; and means for manipulating the plantar contour.

69. The apparatus of claim 68 wherein said manipulating means is formed within said integral container.

70. The apparatus of claim 68 wherein said manipulating means is formed within said carrier.

* * * * *